(12) United States Patent
Bonassar et al.

(10) Patent No.: US 11,812,939 B2
(45) Date of Patent: Nov. 14, 2023

(54) DEVICE AND SYSTEM FOR REPAIRING INTERVERTEBRAL DISC HERNIATION AND METHODS OF USE

(71) Applicant: CORNELL UNIVERSITY, Ithaca, NY (US)

(72) Inventors: Lawrence J. Bonassar, Ithaca, NY (US); Roger Hartl, New York, NY (US); Monika McCarter, Monroe, CT (US); Anny Cunha-Gavidia, Lancaster, MA (US); Michael Messina, Washingtonville, NY (US); Gayathri Shibu, Ithaca, NY (US); Si Chen, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 349 days.

(21) Appl. No.: 16/614,072

(22) PCT Filed: May 15, 2018

(86) PCT No.: PCT/US2018/032769
§ 371 (c)(1),
(2) Date: Nov. 15, 2019

(87) PCT Pub. No.: WO2018/213310
PCT Pub. Date: Nov. 22, 2018

(65) Prior Publication Data
US 2021/0153854 A1    May 27, 2021

Related U.S. Application Data

(60) Provisional application No. 62/506,111, filed on May 15, 2017.

(51) Int. Cl.
*A61B 17/70* (2006.01)
*A61B 17/88* (2006.01)
(Continued)

(52) U.S. Cl.
CPC .... *A61B 17/00491* (2013.01); *A61B 17/7061* (2013.01); *A61B 17/8833* (2013.01);
(Continued)

(58) Field of Classification Search
CPC .......... A61B 2017/005; A61B 17/7061; A61B 17/8833; A61B 17/8836
See application file for complete search history.

(56) References Cited

U.S. PATENT DOCUMENTS 5,445,608 A     8/1995   Chen et al.
5,480,409 A  *  1/1996   Riza .................. A61B 17/2909
                                                      606/205

(Continued)

FOREIGN PATENT DOCUMENTS

WO      2016/166350 A2    10/2016

OTHER PUBLICATIONS

International Search Report and Written Opinion for corresponding Application No. PCT/US2018/032769 (dated Jul. 11, 2018).

(Continued)

*Primary Examiner* — Nicholas W Woodall
(74) *Attorney, Agent, or Firm* — Troutman Pepper Hamilton Sanders LLP (Rochester)

(57) ABSTRACT

A device comprising a housing including a palm portion, a sheath portion extending from one end of the palm portion, and a slot comprising an adjustable platform capable of receiving a syringe and a needle connected to the syringe with the needle resting in the sheath portion. A trigger mechanism is connected to the adjustable platform. Adjustment of the trigger mechanism in a first direction moves the platform along the slot toward the sheath portion and adjustment of the bidirectional trigger mechanism in a second direction moves the platform away from the sheath. A light element is connected to the housing and is capable (Continued)

of directing light along the sheath portion away from the palm portion. A power source is electrically coupled to the light element to provide electrical power to the light element. Also disclosed is a system comprising the device, as well as methods of using the device.

21 Claims, 9 Drawing Sheets

(51) Int. Cl.
*A61B 17/00* (2006.01)
*A61B 17/56* (2006.01)
(52) U.S. Cl.
CPC ............. *A61B 2017/005* (2013.01); *A61B 2017/00734* (2013.01); *A61B 2017/564* (2013.01)

(56) References Cited

U.S. PATENT DOCUMENTS

| | | | |
|---|---|---|---|
| 5,674,921 A * | 10/1997 | Regula | B33Y 80/00 528/80 |
| 5,893,488 A * | 4/1999 | Hoag | A61B 17/8822 222/391 |
| 6,056,728 A * | 5/2000 | von Schuckmann | A61M 5/204 604/207 |
| 6,187,048 B1 | 2/2001 | Milner et al. | |
| 6,387,977 B1 | 5/2002 | Sawhney et al. | |
| 6,488,665 B1 | 12/2002 | Severin et al. | |
| 6,517,847 B2 | 2/2003 | Dow et al. | |
| 7,427,295 B2 | 9/2008 | Ellman et al. | |
| 7,720,533 B2 | 5/2010 | Behravesh et al. | |
| 7,771,476 B2 | 8/2010 | Justis et al. | |
| 8,029,511 B2 | 10/2011 | Bowman et al. | |
| 8,337,557 B2 | 12/2012 | Collins et al. | |
| 8,357,147 B2 | 1/2013 | Burkinshaw et al. | |
| 8,632,524 B2 | 1/2014 | Trieu et al. | |
| 8,734,460 B2 | 5/2014 | Rabiner et al. | |
| 8,784,378 B2 | 7/2014 | Weinandy | |
| 2001/0046652 A1 | 11/2001 | Ostler et al. | |
| 2002/0092871 A1 | 7/2002 | Rickard et al. | |
| 2004/0097927 A1 | 5/2004 | Yeung et al. | |
| 2005/0026103 A1 | 2/2005 | Wasylucha | |
| 2005/0209602 A1 | 9/2005 | Bowman et al. | |
| 2005/0261633 A1 * | 11/2005 | Khalaj | A61M 5/20 604/181 |
| 2006/0287726 A1 | 12/2006 | Segal et al. | |
| 2007/0073275 A1 * | 3/2007 | Conston | A61F 9/00781 606/6 |
| 2007/0162135 A1 | 7/2007 | Segal et al. | |
| 2007/0173943 A1 | 7/2007 | Dulak et al. | |
| 2008/0103564 A1 | 5/2008 | Burkinshaw et al. | |
| 2010/0262188 A1 * | 10/2010 | Rabiner | A61B 17/7013 606/249 |
| 2012/0303036 A1 | 11/2012 | Truckai et al. | |
| 2015/0230900 A1 | 8/2015 | Gente et al. | |
| 2015/0335369 A1 | 11/2015 | Truckai et al. | |
| 2016/0303284 A1 | 10/2016 | Borde et al. | |

OTHER PUBLICATIONS

Kumar et al., "Stem Cell Delivery With Polymer Hydrogel for Treatment of Intervertebral Disc Degeneration: From 3D Culture to Design of the Delivery Device for Minimally Invasive Therapy," Cell Transplantation 25:2213-2220 (2016).

* cited by examiner

DEVICE AND SYSTEM FOR REPAIRING INTERVERTEBRAL DISC HERNIATION AND METHODS OF USE

This application is a national stage application under 35 U.S.C. § 371 of PCT Application No. PCT/US2018/032769, filed May 15, 2018, which claims the benefit of U.S. Provisional Patent Application Ser. No. 62/506,111, filed May 15, 2017, which are hereby incorporated by reference in their entirety.

FIELD OF THE INVENTION

The present invention relates to devices and systems for repairing invertebral disc herniation. The present invention also relates to surgical methods of use of the devices and systems.

BACKGROUND OF THE INVENTION

Low back pain is often a result of a bulging or herniated intervertebral disc ("IVD"). Partial discectomies alleviate the pain of a damaged IVD; however, the resulting annular defect is often left untreated. This increases the likeliness of recurrent disc herniations through the open defect. Annulus repair strategies have been devised to address a range of defects in damaged annulus fibrosus ("AF") tissue. These therapies aim to mechanically close lesions in the AF to prevent prolapse and perhaps slow or inhibit degeneration.

Repair of annular defects could significantly improve treatment of degenerative spinal diseases (Bron et al., "Repair, Regenerative and Supportive Therapies of the Annulus Fibrosus: Achievements and Challenges," Eur. Spine J. 18:301-13 (2009)). Open defects compromise the ability of the AF to contain nuclear tissue in the disc space, thereby increasing the likelihood of reherniation and progressive degeneration after discectomies (Lebow et al., "Asymptomatic Same-Site Recurrent Disc Herniation After Lumbar Discectomy: Results of a Prospective Longitudinal Study with 2-Year Serial Imaging," Spine 36:2147-51 (2011); Ambrossi et al., "Recurrent Lumbar Disc Herniation After Single-Level Lumbar Discectomy: Incidence and Health Care Cost Analysis," Neurosurgery 65:574-8 (2009); McGirt et al., "A Prospective Cohort Study of Close Interval Computed Tomography and Magnetic Resonance Imaging After Primary Lumbar Discectomy: Factors Associated with Recurrent Disc Herniation and Disc Height Loss," Spine 34:2044-51 (2009); Carragee et al., "A Prospective Controlled Study of Limited Versus Subtotal Posterior Discectomy: Short-Term Outcomes in Patients with Herniated Lumbar Intervertebral Discs and Large Posterior Anular Defect," Spine 31:653-7 (2006); Carragee et al., "Clinical Outcomes After Lumbar Discectomy for Sciatica: The Effects of Fragment Type and Anular Competence," J. Bone Joint Surg. Am. 85-A:102-8 (2003)). Furthermore, there has been concern that annular puncture for therapeutic or diagnostic procedures accelerates the progression of degenerative disc disease and promotes nuclear tissue extrusion (Carragee et al., "2009 ISSLS Prize Winner: Does Discography Cause Accelerated Progression of Degeneration Changes in the Lumbar Disc: A Ten-Year Matched Cohort Study," Spine 34:2338-45 (2009)). Successful treatment of puncture defects could inhibit these degenerative changes.

Annular defects persist because of the very limited intrinsic healing capability of the AF, which does not significantly improve upon simple mechanical closure (Bron et al., "Repair, Regenerative and Supportive Therapies of the Annulus Fibrosus: Achievements and Challenges," Eur. Spine J. 18:301-13 (2009); Melrose et al., "Recent Advances in Annular Pathobiology Provide Insights into Rim-Lesion Mediated Intervertebral Disc Degeneration and Potential New Approaches to Annular Repair Strategies," Eur. Spine J. 17:1131-48 (2008); Bron et al., "Biomechanical and In Vivo Evaluation of Experimental Closure Devices of the Annulus Fibrosus Designed for a Goat Nucleus Replacement Model," Eur. Spine J. 19:1347-55 (2010); Fazzalari et al., "Mechanical and Pathologic Consequences of Induced Concentric Anular Tears in an Ovine Model," Spine 26:2575-81 (2001); Hampton et al., "Healing Potential of the Anulus Fibrosus," Spine 14:398-401 (1989)). As a result, several research groups have investigated using biological materials for annular repair.

Tissue-engineered fibrin hydrogels are being developed for annulus repair. Such uses have been studied by one group (Vadala et al., "Bioactive Electrospun Scaffold for Annulus Fibrosus Repair and Regeneration," Eur. Spine J. 21(suppl 1):520-6 (2012)) using tissue-engineered AF constructs in vitro and by another group (Ledet et al., "Small Intestinal Submucosa for Anular Defect Closure: Long-Term Response in an In Vivo Sheep Model," Spine 34:1457-63 (2009)) using small intestinal submucosa in vivo. Implanted submucosa tissue reduced degenerative changes after annulotomy in sheep spine. Schek et al., "Genipin-Crosslinked Fibrin Hydrogels as a Potential Adhesive to Augment Intervertebral Disc Annulus Repair," Eur. Cell. Mater. 21:373-83 (2011) studied injectable biomaterials with genipin cross-linked fibrin hydrogels. Fibrin integrated with sections of human AF tissue, showing promising biomechanical and cell-seeding properties in vitro. Injectable high-density collagen ("HDC") gels were tested and it was found that HDC can partially restore mechanical function to a needle-punctured rat-tail AF in vitro (Borde et al., "Repair of Defects in the Rat Tail Annulus Fibrosus Using Injectable High Density Collagen Gels," Paper presented at: Orthopedic Research Society, Annual Meeting; San Francisco, Calif. (2012)). However, no studies have reported the use of injectable biomaterials to treat annular defects in vivo.

Methods have been proposed for repairing disc herniations using hydrogel delivery and subsequent cross-linking. However, existing solutions address the need for either hydrogel delivery or light emission, but not both. Further, existing devices are not capable of providing both functions in conjunction for intervertebral disc herniation procedures.

The present invention is directed to overcoming these and other deficiencies in the art.

SUMMARY OF THE INVENTION

One aspect of the present invention relates to a device comprising a housing that includes a palm portion and a sheath portion extending from one end of the palm portion. The housing also comprises a slot comprising an adjustable platform capable of receiving a syringe and a needle connected to the syringe, such that when the syringe is positioned on the adjustable platform, the needle rests in the sheath portion of the housing. A bidirectional trigger mechanism is connected to the adjustable platform. Adjustment of the bidirectional trigger mechanism in a first direction moves the platform along the slot toward the sheath portion and adjustment of the bidirectional trigger mechanism in a second direction moves the platform along the slot away from the sheath. A light element is connected to the housing and is capable of directing light along the sheath portion away from the palm portion. A power source is electrically coupled to the light element to provide electrical power to the light element.

Another aspect of the present invention relates to a system comprising the device of the present invention. The system also includes a syringe comprising a reservoir, a plunger, and a needle. When the reservoir is positioned on the adjustable platform of the device the needle rests in the sheath portion.

A further aspect of the present invention relates to a surgical method. The method involves providing the system of the present invention, wherein the reservoir of the syringe comprises a photo-curable material. The sheath portion is positioned proximal to a surgical site. The bidirectional trigger mechanism is adjusted in a direction to move the platform along the slot toward the sheath portion, such that the needle extends beyond the sheath. The plunger is pressed to extrude the material out of the needle and onto the surgical site. The light element is activated to cure the material.

Yet another aspect of the present invention relates to a device comprising a housing that includes a palm portion and a sheath portion extending from one end of the palm portion. The sheath portion has a proximal end connected to the palm portion and an adjustable distal end, the adjustable distal end being retractable. The housing further includes a slot capable of receiving a syringe and a needle connected to the syringe, such that when the syringe is positioned in the slot, the needle rests in the sheath portion. A bidirectional trigger mechanism is connected to the adjustable distal end of the sheath portion. Movement of the bidirectional trigger mechanism in a first direction retracts the adjustable distal end and movement of the bidirectional trigger mechanism in a second direction extends the adjustable distal end. A light element is connected to the housing and is capable of directing light along the sheath portion away from the palm portion. A power source is electrically coupled to the light source to provide electrical power to the light element.

An additional aspect of the present invention relates to a surgical method. The method includes providing the system of the present invention wherein the reservoir comprises a photo-curable material. The sheath portion is positioned proximal to a surgical site. The bidirectional trigger mechanism is adjusted in a direction to retract the adjustable distal end, such that the needle is exposed beyond the sheath. The plunger is pressed to extrude the material out of the needle and onto the surgical site. The light element is activated to cross-link the material.

The present invention advantageously provides devices and methods that may be employed in minimally invasive spinal surgery. The devices, systems, and methods of the present invention can be utilized to provide for delivery and curing of a photo-cross-linkable hydrogel for the purpose of sealing surgical spinal defects. The systems of the present invention provides a single device that provides for both the delivery and curing of a hydrogel. The devices, systems, and methods provide clinical feasibility for the controlled delivery and activation of a hydrogel solution to initiate tissue regeneration within an intervertebral disc injury site. The devices and systems further allow the surgeon to manually engage with the device for controlled operation of all of the components of the device. As such, the devices, systems, and methods of the present invention can play an essential role in significantly improving the standard of care for discectomy procedures in a clinical setting.

DETAILED DESCRIPTION OF THE INVENTION

The present invention relates to devices and systems for repairing invertebral disc herniation. The present invention also relates to surgical methods of use of the devices and systems.

One aspect of the present invention relates to a device comprising a housing that includes a palm portion and a sheath portion extending from one end of the palm portion. The housing also comprises a slot comprising an adjustable platform capable of receiving a syringe and a needle connected to the syringe, such that when the syringe is positioned on the adjustable platform, the needle rests in the sheath portion of the housing. A bidirectional trigger mechanism is connected to the adjustable platform. Adjustment of the bidirectional trigger mechanism in a first direction moves the platform along the slot toward the sheath portion and adjustment of the bidirectional trigger mechanism in a second direction moves the platform along the slot away from the sheath. A light element is connected to the housing and is capable of directing light along the sheath portion away from the palm portion. A power source is electrically coupled to the light element to provide electrical power to the light element.

Figure 1A:
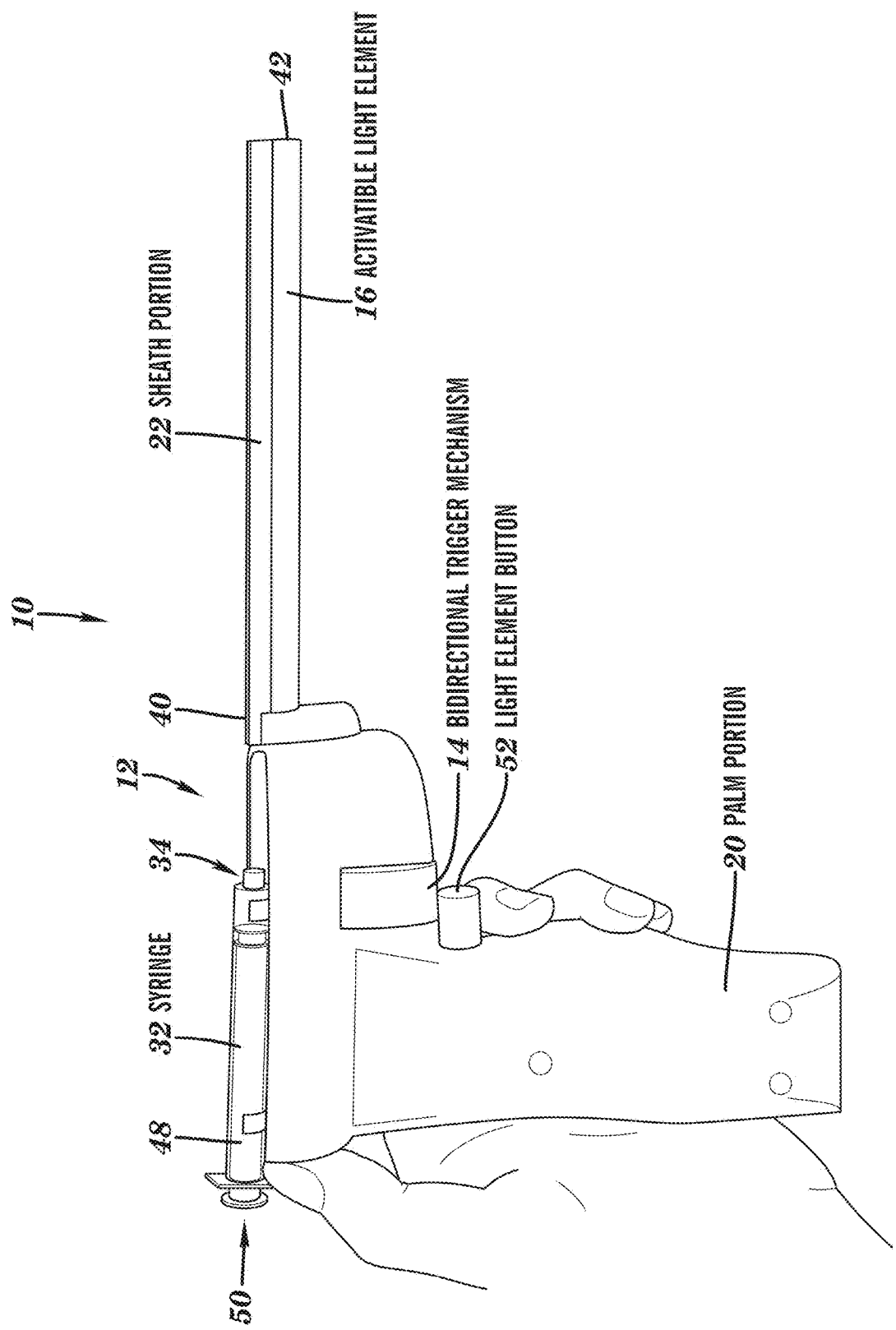
FIG. 1A shows an exemplary system of the present invention including an exemplary device for repairing invertebral disc herniation and a syringe.
Figure 2:
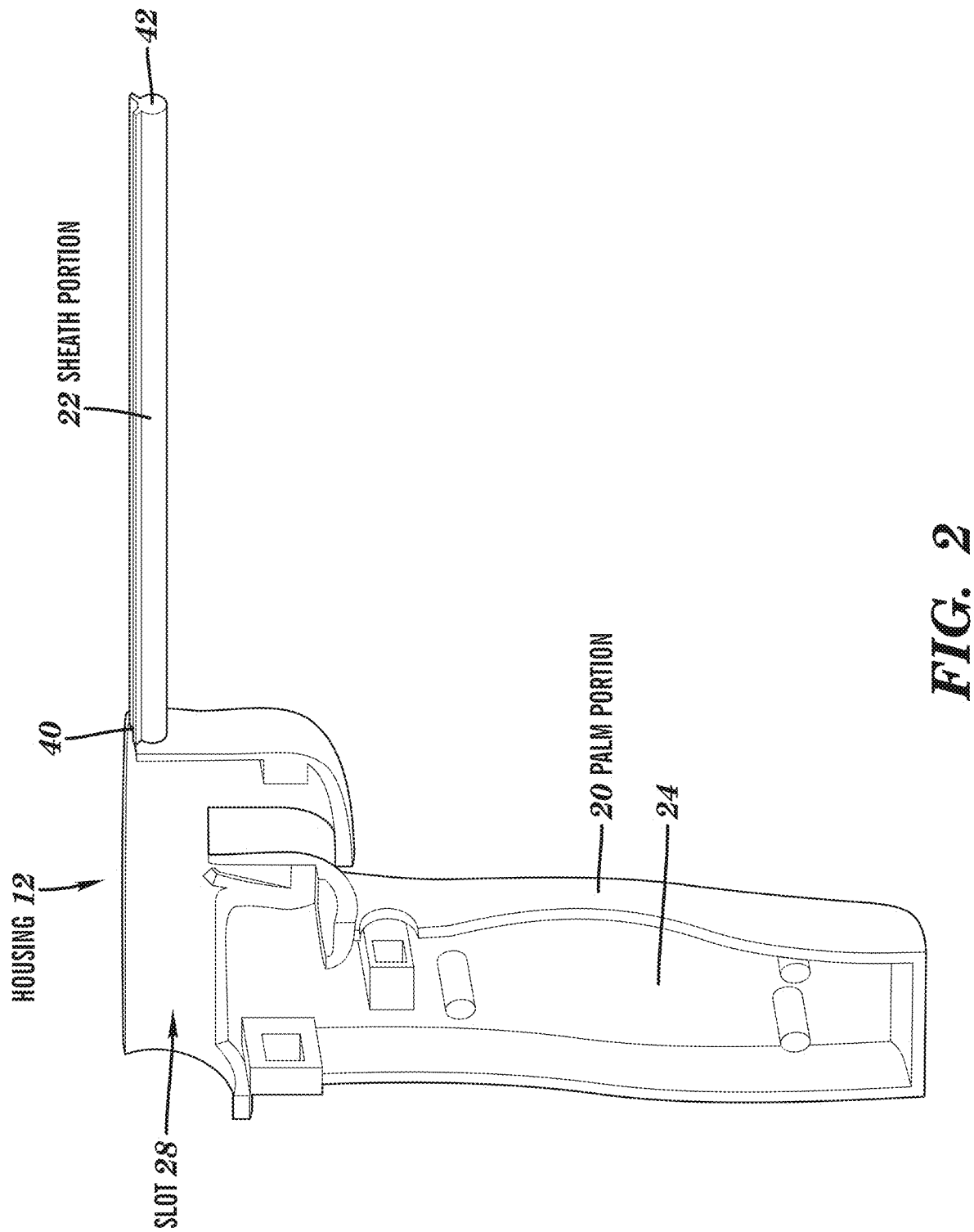
FIG. 2 shows the exemplary device for repairing invertebral disc herniation of the present invention with a cover portion removed.
Figure 3:
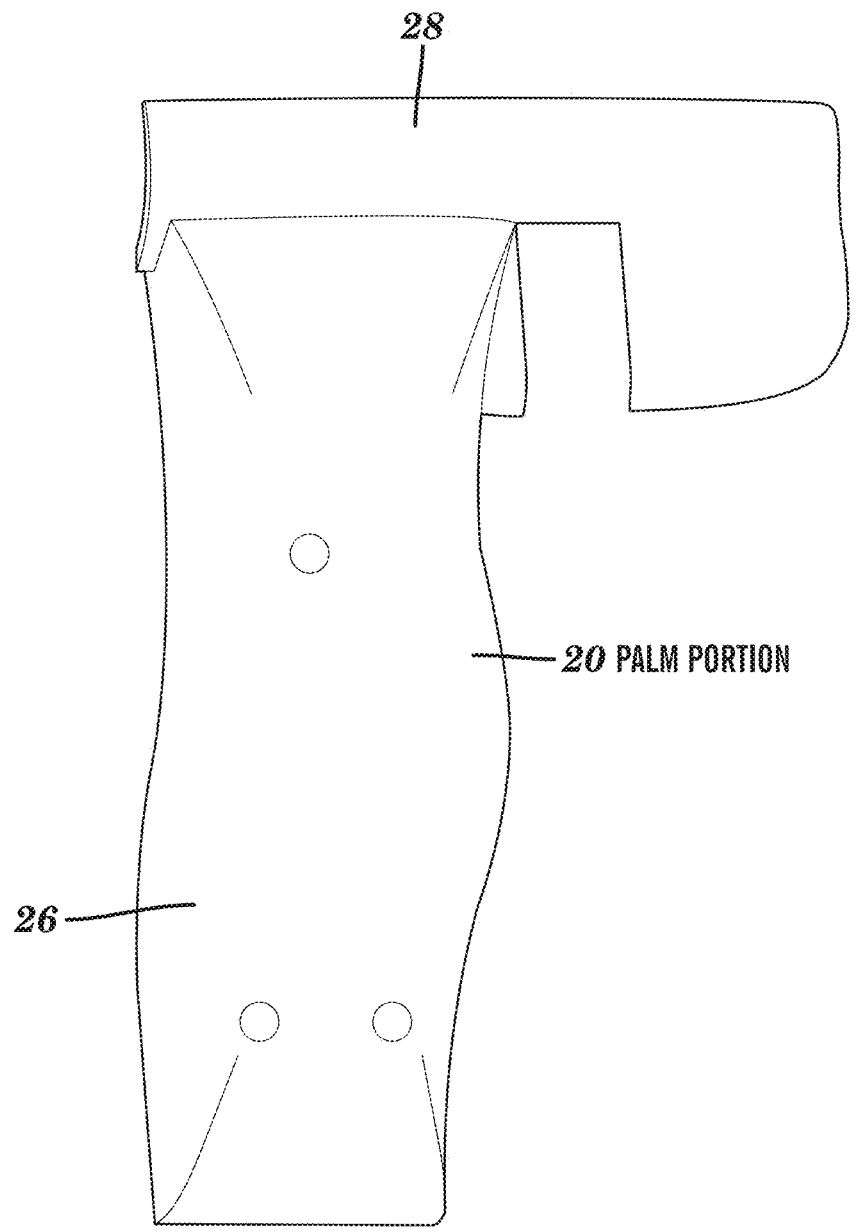
FIG. 3 shows a palm portion of the exemplary device for repairing invertebral disc herniation of the present invention.
Figure 4:
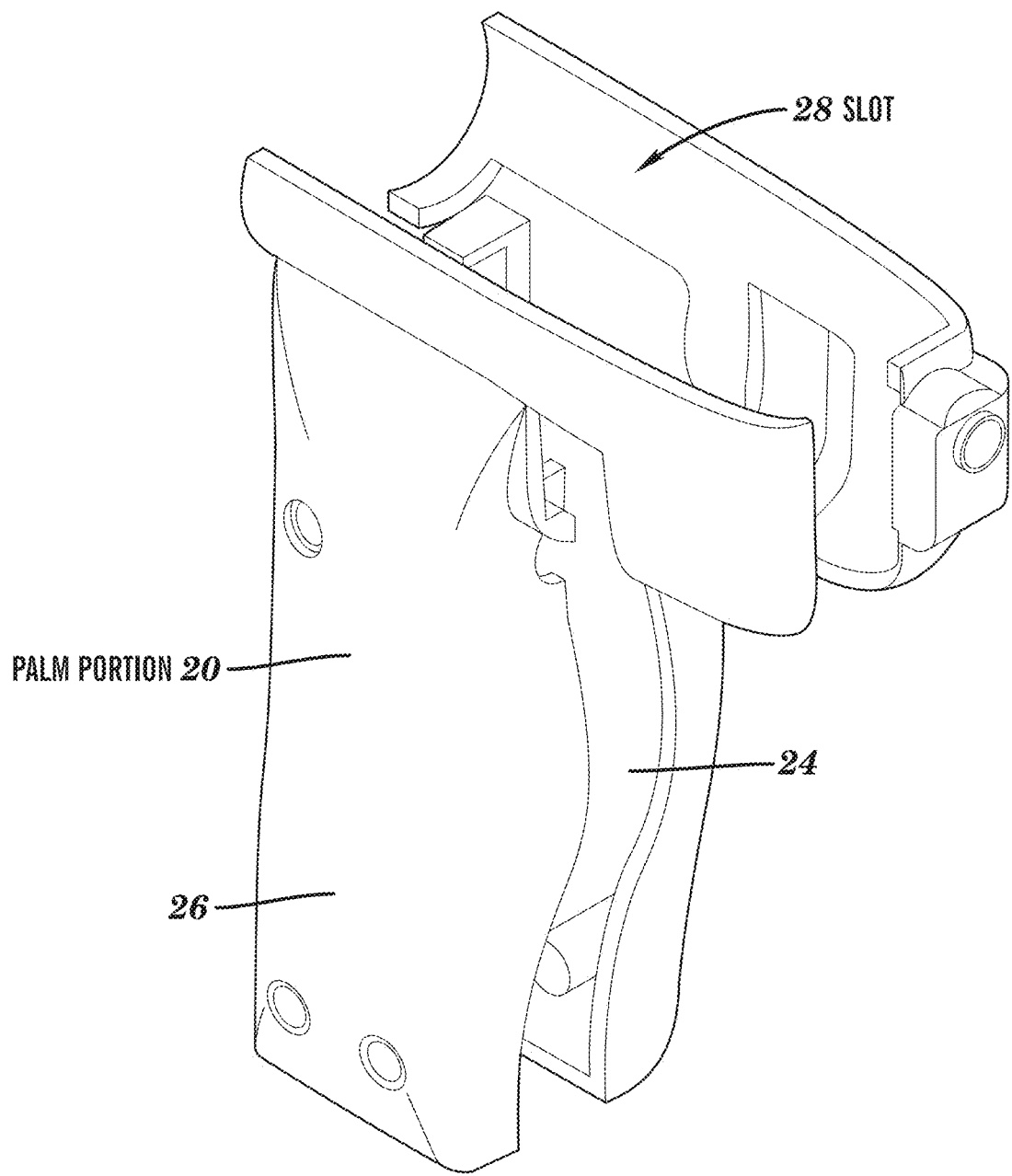
FIG. 4 is an exploded perspective view of the palm portion of the exemplary device for repairing invertebral disc herniation of the present invention.

FIGS. 1A-6 show images of a first embodiment of device 10 of the present invention. Referring more specifically to FIGS. 1A and 1B, device 10 includes housing 12, trigger mechanism 14, light element 16, and power source 18 (as shown in FIG. 4), although device 10 may have other types and/or numbers of elements or components in other combinations. Device 10 of the present invention provides a single device that combines a syringe delivery mechanism and a light element for use in the repair of invertebral disc herniations. Device 10 is capable of efficiently providing for both the delivery and curing of hydrogel for the purpose of sealing surgical spinal defects, by way of example only. Device 10 can be easily handled and controlled by a user during minimally invasive surgical procedures.

Housing 12 includes palm portion 20 and sheath portion 22. In this example, housing 12 is formed of a plastic material, although housing 12 may be formed of other materials, such as other polymers or metals for example. Housing 12 can be formed using any suitable techniques known in the art of fabricating medical devices, such as injection molding or 3D printing. Housing 12 can be fabricated in an ISO 8 or Class 100K certified clean room to provide for a device that may be employed in sterile surgical settings. Housing 12 can also be sterilized using treatment with ethylene oxide followed by vacuum sealant packaging that keeps housing 12 sterile prior to use.

Referring now more specifically to FIGS. 2-4, in this example, palm portion 20 of housing 12 is formed of a compartment 24 and a cover 26, although in other examples palm portion 20 of housing 12 could be formed as single unitary construction. Compartment 24 houses the working elements of device 10, including trigger mechanism 14. In other examples, light element 16 and power source 18 may also be located in compartment 24. Cover 26 provides a closure for housing 12 and may be coupled to compartment 24 using an attachment mechanism such as screws or clips, although any suitable attachment mechanism may be utilized to couple compartment 24 and cover 26. In another example, cover 26 may include a removal door portion that allows access solely to power source 18 for removal and replacement of power source 18.

Referring again to FIGS. 1A, 1B, and 2, palm portion 20 of housing 12 is coupled to proximal end 40 of sheath portion 22. Palm portion 20 provides a handle for device 10 and is configured to allow a user to operate device 10 using a single hand. Palm portion 20 may include one or more ergonomic features to allow the user to comfortably hold and operate device 10.

Figure 1B:
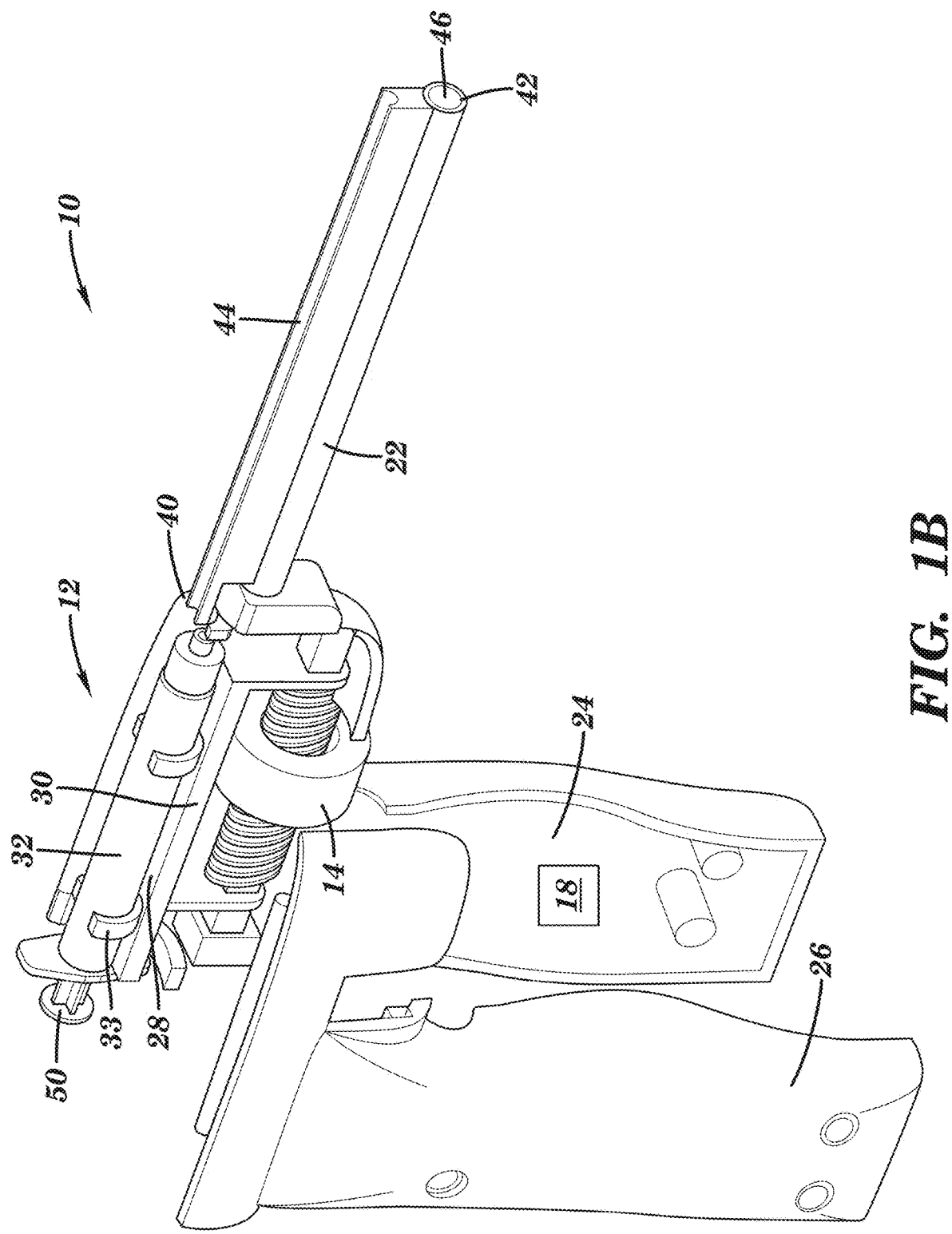
FIG. 1B is an exploded perspective view of the exemplary system of the present invention as shown in FIG. 1A.
Figure 5:
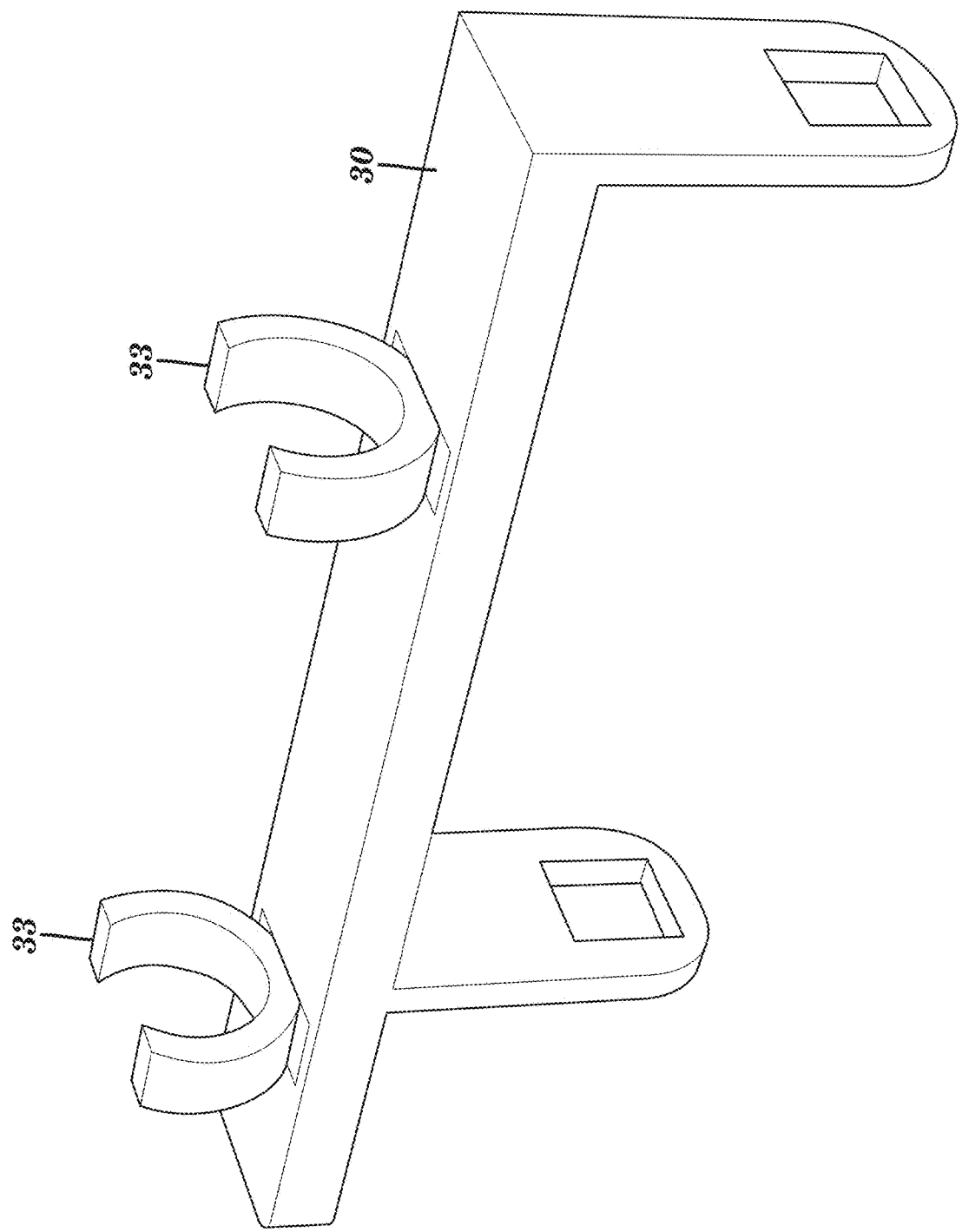
FIG. 5 shows a perspective view of an adjustable platform that can be located in the palm portion of the exemplary device for repairing invertebral disc herniation of the present invention.

Palm portion 20 provides slot 28 (see FIGS. 2-4) that is located within housing 12. Slot 28 is configured to receive an adjustable platform 30, such that adjustable platform 30 (see FIGS. 5 and 7) is linearly moveable along slot 28. An exemplary adjustable platform 30 that may be located and moveable within slot 28 is shown in FIG. 5. Adjustable platform 30 is to receiving syringe 32. Adjustable platform 30 can have one or more features, such as clips 33, that allow for coupling of syringe 32 to adjustable platform 30, although adjustable platform 30 can have other elements such as semicircular elements that receive syringe 32 in a pressure fit, or hoops for syringe 32 that may be manually tightened to hold syringe 32 in place. When syringe 32 is positioned on adjustable platform 30, needle 34 rests in sheath portion 22 of housing 12 as illustrated in FIGS. 1A and 1B and as described further below.

Figure 7:
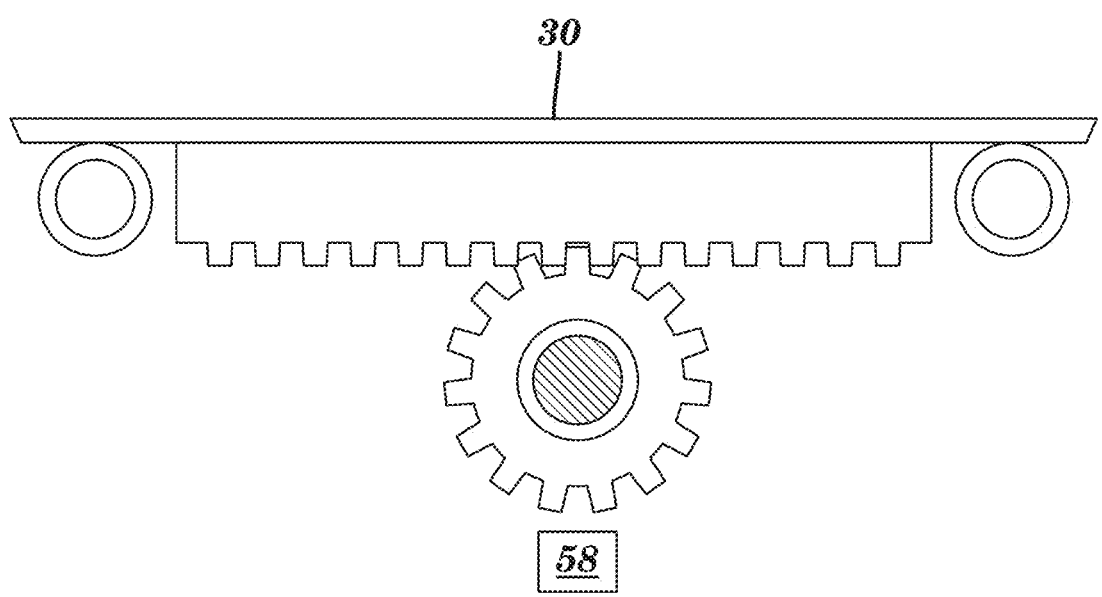
FIG. 7 shows a rack and pinion that may be used as a linear actuator in the exemplary device for repairing invertebral disc herniation of the present invention.
Figure 8:
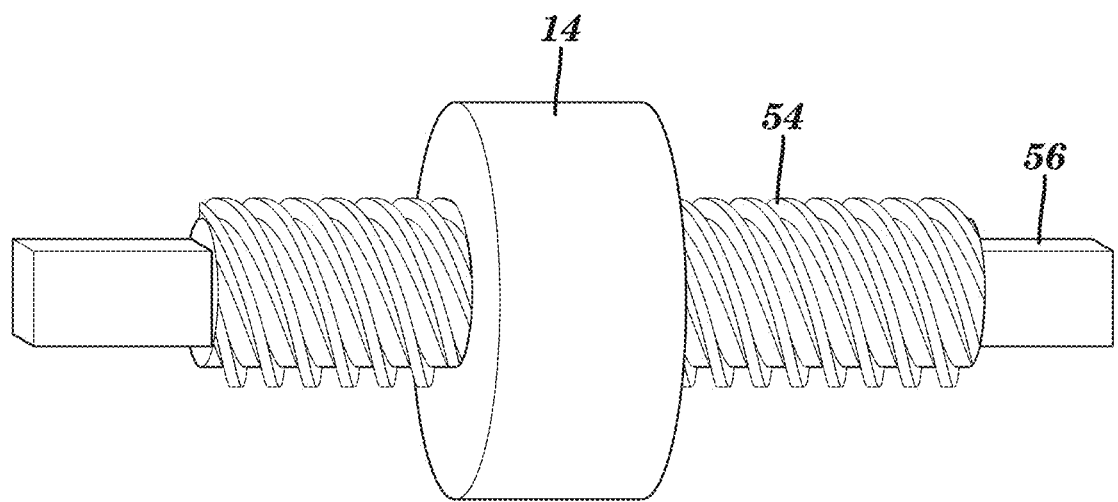
FIG. 8 shows a threaded rod and nut that may be used as a linear actuator in the exemplary device for repairing invertebral disc herniation of the present invention.

Adjustable platform 30 is coupled to a linear actuator that moves adjustable platform 30 based on movement of trigger mechanism 14 as described in further detail below. In one example, adjustable platform 30 is a rack of a rack and pinion structure as shown in FIG. 7 that allows for linear actuation of adjustable platform 30. In this example, the rack and pinion structure can be coupled to trigger mechanism 14 through a ratchet to allow linear actuation of the rack (i.e., adjustable platform 30). Alternatively, the rack and pinion may be coupled directly to a thumbwheel that serves as trigger mechanism 14 to move the rack (i.e., adjustable platform 30). In either of these examples, locking mechanism 58 may be employed on adjustable platform 30 to prevent motion of adjustable platform 30 when the user wants to maintain the position of syringe 32 for delivery of the payload, or during insertion and/or removal of device 10 from the surgical site. In another example, adjustable platform 30 is coupled to lead screw 54 mounted on guiderail 56, as shown in FIG. 8, that can be driven by a nut that serves as trigger mechanism 14. This example may not require a locking mechanism as friction forces between the nut and screw can prevent unwanted linear motion.

Figure 6:
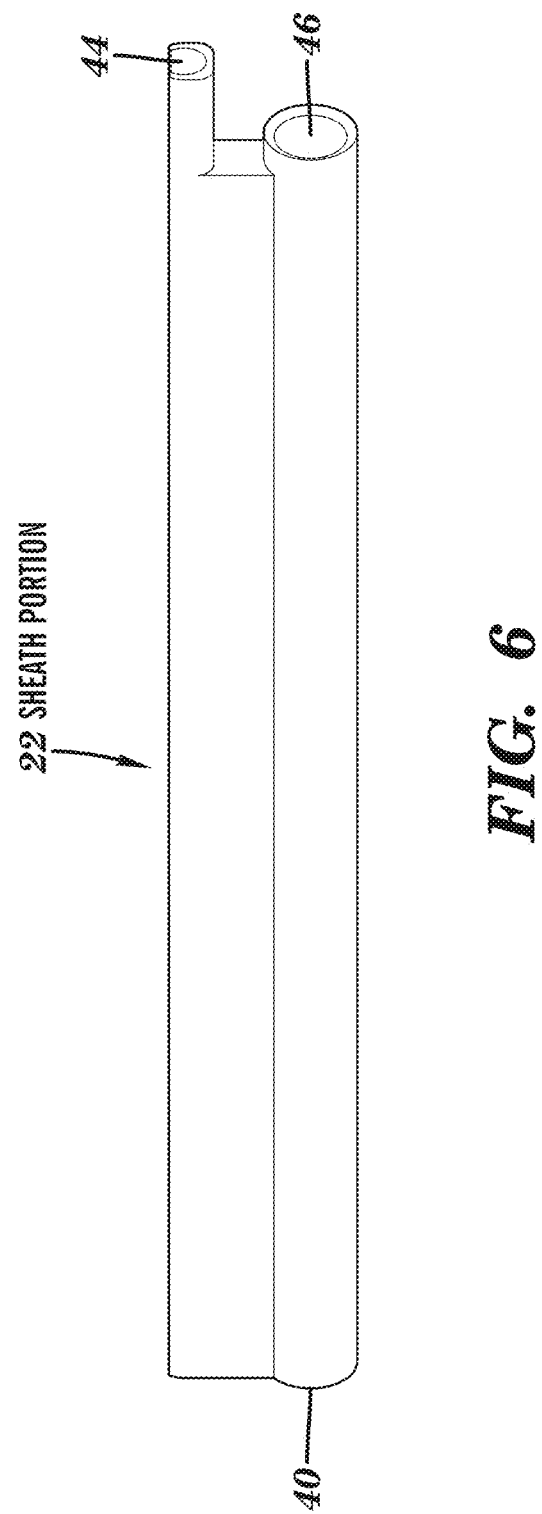
FIG. 6 shows a sheath portion of the exemplary device for repairing invertebral disc herniation of the present invention.

Referring now to FIGS. 1, 2, and 6, sheath portion 22 extends longitudinally between proximal end 40 to distal end 42. Sheath portion 22 is coupled to palm portion 20 at proximal end 40. Sheath portion 22 includes first channel 44 and second channel 46. First channel 44 is configured, during use of device 10, to receive needle 34, which is connected to syringe 32, when syringe 32 is located in palm portion 20. First channel 44 guides the movement of needle 34 from a position within sheath portion 22 to an actuated position with at least a portion of needle 34 extended beyond distal end 42 of sheath portion 22. Sheath 22 serves to protect tissue around the targeted delivery site when needle 34 is recessed in first channel 44. In this example, first channel 44 is a semicircular open channel configured to receive and guide needle 34. Second channel 46 is configured to house light element 16, although light element 16 can be housed in other locations, such as in compartment 24 of palm portion 20, or external to device 10. In this example, second channel 46 is a tube configured to receive a fiber optic cable, or a bundle of fiber optic cables, that are part of light element 16 to provide a more focused source of light.

Referring again to FIGS. 1A and 1B, trigger mechanism 14 is located within and extends from palm portion 20 of housing 12 and provides a mechanism to move syringe 32 (through movement of adjustable platform 30) to extend and expose needle 34 from sheath portion 22. Trigger mechanism 14 is connected to adjustable platform 30 and controls movement of adjustable platform 30. Trigger mechanism 14 extends from palm portion 20 so that a user can easily operate trigger mechanism 14 while holding palm portion 20. Trigger mechanism 14 provides for controlled delivery of needle 34 to the surgical site. The motion of adjustable platform 30, and movement of syringe 32 and needle 34 out of the sheath portion 22, can be regulated using trigger mechanism 14. The range of motion of needle 34 based on activation of trigger mechanism 14 can be customized based on the desired application.

In this example, trigger mechanism 14 is bidirectional such that movement of trigger mechanism 14 in a first direction moves adjustable platform 30 along slot 28 toward sheath portion 22. By way of example, movement of trigger mechanism 14 in the first direction may involve rotating trigger mechanism 14, although in other examples trigger mechanism 14 may operate in the fashion of a trigger on a firearm. Adjustment of trigger mechanism 14 in a second direction, in this example opposite to the first direction, moves adjustable platform 32 along slot 30 away from sheath portion 20 of housing 12. By way of example, movement of trigger mechanism 14 in the second direction may involve rotating trigger mechanism 14.

Trigger mechanism 14 is coupled to and drives a linear actuator to move syringe 32 when installed in device 10. In one example, trigger mechanism 14 is coupled to a ratchet coupled to a pinion of a rack and pinion system, the rack of which provides adjustable platform 30 (see FIG. 7). In another example, trigger mechanism 14 is a thumbwheel that drives the rack and pinion system directly. In yet another example, trigger mechanism 14 is a nut coupled to a lead screw coupled to a guiderail that serves as adjustable platform 30 such that rotation of the nut provides movement of the lead screw and the guiderail (see FIG. 8).

Light element 16 is located within housing 12. In one example, light element 16 is located at distal end 42 of sheath portion 22 in second channel 46, although in other examples, light element 16 may be located in other areas of housing 12, such as in compartment 24 of palm portion 20. Light element 16 is capable of directing light out of sheath portion 22 to a site of delivery of a curable hydrogel, as described in further detail below. Light element 16 can be activated using button 52 located on palm portion 20.

Light element 16 can be coupled to a fiber optic bundle to deliver light from light element 16 to a surgical site through second channel 46 in sheath portion 22. In this example, the fiber optic bundle is capable of focusing light from light element 16 along sheath portion 22. Use of a fiber optic bundle allows for the application of focused light on the delivery site with minimal loss, which decreases energy loss and allows intensity of the light to be attenuated. The type of light, including wavelength and intensity of the light, delivered from light element 16 varies upon the application, i.e., the curing conditions of the hydrogel employed. Various light elements 16 may be employed based on hydrogel curing conditions known in the art. In one example, light element 16 provides a blue light of approximately 455 nm wavelength to trigger activation of a photo-cross-linkable hydrogel, by way of example only.

Power source 18 is electrically coupled to light element 16 to provide electrical power for the operation of light element 16. Power source 18 can be located in compartment 24 of palm portion 20, although an external power source could also be employed. In one example, power source 18 is a battery, although other types and/or numbers of power sources may be employed as power source 18. Power source 18 could be an internal battery pack with disposable batteries, or a reusable, rechargeable battery pack that can be inserted and removed from compartment 24.

Yet another aspect of the present invention relates to a device comprising a housing that includes a palm portion and a sheath portion extending from one end of the palm portion. The sheath portion has a proximal end connected to the palm portion and an adjustable distal end, the adjustable distal end being retractable. The housing further includes a slot capable of receiving a syringe and a needle connected to the syringe, such that when the syringe is positioned in the slot, the needle rests in the sheath portion. A bidirectional trigger mechanism is connected to the adjustable distal end of the sheath portion. Movement of the bidirectional trigger mechanism in a first direction retracts the adjustable distal end and movement of the bidirectional trigger mechanism in a second direction extends the adjustable distal end. A light element is connected to the housing and is capable of directing light along the sheath portion away from the palm portion. A power source is electrically coupled to the light source to provide electrical power to the light element.

In another example, sheath portion 22 includes distal end 42 that is adjustable to retract a portion of distal end 42 to expose needle 34 located in sheath portion 22. This example is the same in structure and operation as the example described above, except as noted below.

In this example, trigger mechanism 14 is coupled to the adjustable distal end 42 of sheath portion 22. Movement of trigger mechanism 14 in a first direction causes the adjustable distal end 42 to retract to expose needle 34 located therein. Movement of trigger mechanism 14 in a second direction, opposite to the first direction, causes adjustable distal end 42 of sheath portion 22 to extend the adjustable distal end 42 to cover needle 34 located therein to provide protection to the surgical area from needle 34. In this example, syringe 32 is located on a platform within palm portion 20 that is static, as opposed to adjustable platform 30 as described above and movement of distal end 42 of sheath portion 22 serves to selectively expose and cover needle 34.

Another aspect of the present invention relates to a system comprising a device of the present invention. The system also includes a syringe comprising a reservoir, a plunger, and a needle. When the reservoir is positioned on the adjustable platform of the device the needle rests in the sheath portion.

Referring again to FIGS. 1A and 1B, device 10 can be coupled with syringe 32 as described above. Syringe 32 includes reservoir 48 that can be utilized to hold a photo-curable hydrogel, by way of example only. Syringe 32 further includes plunger 50 that can be used to introduce the hydrogel stored in reservoir 48 to a surgical site through needle 34. Syringe 32 may be utilized for the mixing and processing of the hydrogel prior to introduction into device 10. Syringe 32 may be any syringe known in the art. Adjustable platform 30 is configured to receive and hold syringe 32, as described above, during operation of device 10.

A further aspect of the present invention relates to a surgical method. The method involves providing the system of the present invention, wherein the reservoir of the syringe comprises a photo-curable material. The sheath portion is positioned proximal to a surgical site. The bidirectional trigger mechanism is adjusted in a direction to move the platform along the slot toward the sheath portion, such that the needle extends beyond the sheath. The plunger is pressed to extrude the material out of the needle and onto the surgical site. The light element is activated to cure the material.

An additional aspect of the present invention relates to a surgical method. The method includes providing the system of the present invention wherein the reservoir comprises a photo-curable material. The sheath portion is positioned proximal to a surgical site. The bidirectional trigger mechanism is adjusted in a direction to retract the adjustable distal end, such that the needle is exposed beyond the sheath. The plunger is pressed to extrude the material out of the needle and onto the surgical site. The light element is activated to cross-link the material.

In one example, the surgical method of the present invention can be used to repair invertebral disc herniation. In particular, device 10 may be utilized during minimally invasive microdiscectomy procedures that amend IVD herniations, although other uses are also contemplated. Intervertebral discs separate the spinal vertebrae from one another and act as natural shock absorbers by cushioning impacts and absorbing the stress and strain transmitted to the spinal column. Intervertebral disc tissues are primarily composed of three regions, the end plates, the annulus fibrosus ("AF") and the nucleus pulposus ("NP"). The annulus fibrosus is a tough collagen-fiber composite that has an outer rim of type I collagen fibers surrounding a less dense fibrocartilage and a transitional zone. These collagen fibers are organized as cylindrical layers. In each layer the fibers are parallel to one another; however, the fiber orientation between layers varies between 30 and 60 degrees. This organization provides support during torsional, bending, and compressive stresses on the spine. The end plates, which are found at the upper and lower surfaces of the disc, work in conjunction with the annulus fibrosus to contain the gel-like matrix of the nucleus pulposus within the intervertebral disc. The nucleus pulposus is made up of a soft matrix of proteoglycans and randomly oriented type II collagen fibers in water. The proteoglycan and water content are greatest at the center of the disc and decrease toward the disc periphery. Disc herniation occurs when the annulus fibrosus structure of an IVD is torn or otherwise damaged.

Device 10 of the present invention can be utilized in microdiscectomy procedures that amend intervertebral disc herniations. Patients who undergo microdiscectomy procedures have high rates of subsequent herniations. The occurrence of subsequent herniations is detrimental to patient health because they elicit the same symptoms as the initial herniation, warranting additional surgical intervention. The discectomy procedure aims to remove bulging material from the nucleus pulposus (the softer, inner portion of the IVD) through a surgical incision in the annulus fibrosus (the stiffer, outer portion of the IVD). Device 10 can be used to accurately deliver hydrogel to the site of the incision in a controlled manner.

During the course of the microdiscectomy procedure, the patient is prone and a 15 mm tube retractor is placed in the posterior in alignment with the IVD of interest. Superficial tissue is cut away between the surgical target and the disc incision site. When the IVD is reached, the external portion of the tissue is cut in order to access the nucleus pulposus. When the bulging material is removed, device 10 can be utilized to deliver and cure a material that acts to seal the surgical defect in the annulus fibrosus as described in further detail below.

The surgical method of the present invention involves the delivery of a composition for a surgical repair, such as repair of a disc herniation, in a controlled manner, as well as cross-linking or curing of the material. For example, the composition may include cells seeded in a gel, such as hydrogel.

A hydrogel can be provided in reservoir 48 of syringe 34. The general preparation of hydrogel-cell compositions is known in the art. See, e.g., U.S. Pat. No. 6,773,713 to Bonassar et al., which is hereby incorporated by reference in its entirety. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. Hydrogels can rapidly solidify to keep the cells evenly suspended within a mold (or around or within another solidified gel) until the gel solidifies. Hydrogels can also be biocompatible, e.g., not toxic to cells suspended in the hydrogel. Suitable hydrogel examples include hydrogels set by exposure to either visible or ultraviolet light, e.g., polyethylene glycol polylactic acid copolymers with acrylate end groups.

Syringe 32, including the hydrogel in reservoir 48 is loaded into device 10 on adjustable platform, such that needle 34 is located within first channel of sheath portion 22. Clips 33 can be used to secure syringe 32 to adjustable platform 30. Next, sheath portion 22 is positioned proximal to a surgical site, such as a surgical incision related to a herniated IVD. A locking mechanism can be employed to avoid movement of needle 34 during movement of device 10 to the surgical site to protect the surrounding tissue. Device 10 is manually operated by the user through palm portion 20, which is ergonomically designed to allow easy control of device 10 using a single hand. With sheath portion 22 in position, trigger mechanism 14 is adjusted by the user in a direction to move adjustable platform 30 along slot 28 toward sheath portion 22. Movement of adjustable platform causes needle 34 to extend beyond sheath portion 22 and into the surgical site. In another example, as described above, movement of trigger mechanism 14 may result in movement of an adjustable distal end 42 of sheath portion 22 to expose needle 34.

The user then activates plunger 50 of syringe 32 by pressing on plunger 50 to extrude the material, such as a hydrogel, out of needle 34 and into the surgical site. The user can then re-sheath needle 34 using trigger mechanism 14. Light element 16 is then activated by the user with device 10 located near the surgical site for a sufficient period of time to cure or cross-link the material, for example to initiate polymerization to seal the surgical defect.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A device comprising:
    a housing comprising:
        a palm portion and a sheath portion extending from one end of the palm portion;
        a slot comprising an adjustable platform capable of receiving a syringe and a needle connected to the syringe, wherein the adjustable platform is configured such that when the syringe is positioned on the adjustable platform, the needle rests in the sheath portion; and
        a bidirectional trigger mechanism positioned proximate the palm portion toward the sheath portion and connected to the adjustable platform, wherein adjustment of the bidirectional trigger mechanism in a first direction moves the adjustable platform and the syringe along the slot toward the sheath portion and, when moved sufficiently in the first direction, extends the needle beyond the sheath portion to expose the needle beyond the sheath portion and adjustment of the bidirectional trigger mechanism in a second direction moves the adjustable platform and the syringe along the slot away from the sheath portion and, when moved sufficiently in the second direction, retracts the needle from being exposed beyond the sheath portion;
    a light element connected to the housing and capable of directing light along the sheath portion away from the palm portion; and
    a power source electrically coupled to the light element to provide electrical power to the light element.

2. The device according to claim 1, wherein the sheath portion comprises a first channel for receiving a needle and a second channel for receiving the light element.

3. The device according to claim 2, wherein the first channel is a semicircular open channel and the second channel is a tube.

4. The device according to claim 1 further comprising:
    a locking mechanism connected to the bidirectional trigger to lock the adjustable platform in place.

5. The device according to claim 1, wherein the adjustable platform further comprises:
    a ratchet connected to a linear motion mechanism.

6. The device according to claim 1 further comprising:
    a fiber optic bundle capable of focusing light from the light element along the sheath portion.

7. The device according to claim 1, wherein the power source is a battery.

8. A system comprising:
    the device according to claim 1 and
    a syringe comprising a reservoir, a plunger, and a needle, wherein when the reservoir is positioned on the adjustable platform the needle rests in the sheath portion.

9. A surgical method comprising:
    providing a system comprising:
        a syringe comprising a reservoir, a plunger, and a needle and
        a device comprising:

a housing comprising:
   a palm portion and a sheath portion extending from one end of the palm portion;
   a slot comprising an adjustable platform capable of receiving the syringe and the needle, wherein when the reservoir is positioned on the adjustable platform the needle rests in the sheath portion, and wherein the reservoir comprises a photo curable material; and
   a bidirectional trigger mechanism positioned proximate the palm portion toward the sheath portion and connected to the adjustable platform, wherein adjustment of the bidirectional trigger mechanism in a first direction moves the adjustable platform and the syringe along the slot toward the sheath portion and, when moved sufficiently in the first direction, extends the needle of the syringe beyond the sheath portion to expose the needle beyond the sheath portion and adjustment of the bidirectional trigger mechanism in a second direction moves the adjustable platform and the syringe positioned along the slot away from the sheath portion and, when moved sufficiently in the second direction, retracts the needle from being exposed beyond the sheath portion;
   a light element connected to the housing and capable of directing light along the sheath portion away from the palm portion; and
   a power source electrically coupled to the light element to provide electrical power to the light element, wherein the reservoir comprises a photo curable material; and
positioning the sheath portion proximal to a surgical site;
adjusting the bidirectional trigger mechanism in a direction to move the adjustable platform along the slot toward the sheath portion, wherein said adjusting extends the needle beyond the sheath portion;
pressing the plunger to extrude the material out of the needle and onto the surgical site; and
activating the light element to cure the material.

10. The method according to claim 9, wherein the surgical site is a herniated disc.

11. The method according to claim 9, wherein the material is a photo-curable hydrogel.

12. A device comprising:
a housing comprising:
   a palm portion and a sheath portion extending from one end of the palm portion, wherein the sheath portion has a proximal end connected to the palm portion and an adjustable distal end, the adjustable distal end being retractable;
   a slot capable of receiving a syringe and a needle connected to the syringe, wherein the slot is configured such that when the syringe is positioned in the slot, the needle rests in the sheath portion;
   a bidirectional trigger mechanism connected to the adjustable distal end of the sheath portion, wherein movement of the bidirectional trigger mechanism in a first direction retracts the adjustable distal end to expose the needle beyond the sheath portion when the syringe is positioned in the slot and movement of the bidirectional trigger mechanism in a second direction extends the adjustable distal end so that the needle is not extended beyond the sheath portion when the syringe is positioned in the slot;
a light element connected to the housing and capable of directing light along the sheath portion away from the palm portion;
a power source electrically coupled to the light source to provide electrical power to the light element.

13. The device according to claim 12, wherein the sheath portion comprises a first channel for receiving a needle and a second channel for receiving the light element.

14. The device according to claim 13, wherein the first channel is a semicircular open channel and the second channel is a tube.

15. The device according to claim 12 further comprising:
   a locking mechanism connected to the bidirectional trigger mechanism to lock the adjustable distal end of the sheath in place.

16. The device according to claim 12 further comprising:
   a fiber optic bundle to focus light from the light element along the sheath portion.

17. The device according to claim 12, wherein the power source is a battery.

18. A system comprising:
the device according to claim 12 and
a syringe comprising a reservoir, a plunger, and a needle, wherein the reservoir is positioned in the slot and the needle rests in the sheath portion.

19. A surgical method comprising:
providing the system of claim 18, wherein the reservoir comprises a photo-curable material;
positioning the sheath portion proximal to a surgical site;
adjusting the bidirectional trigger mechanism in a direction to retract the adjustable distal end, wherein said adjusting exposes the needle beyond the sheath portion;
pressing the plunger to extrude the material out of the needle and onto the surgical site; and
activating the light element to cross-link the material.

20. The method according to claim 19, wherein the surgical site is a herniated disc.

21. The method according to claim 19, wherein the material is a photo-curable hydrogel.

* * * * *

UNITED STATES PATENT AND TRADEMARK OFFICE
CERTIFICATE OF CORRECTION

PATENT NO. : 11,812,939 B2
APPLICATION NO. : 16/614072
DATED : November 14, 2023
INVENTOR(S) : Bonassar et al.

It is certified that error appears in the above-identified patent and that said Letters Patent is hereby corrected as shown below:

In the Claims

At Claim 9, Column 11, Lines 32-33, the words ", wherein the reservoir comprises a photo curable material" should be deleted.

Signed and Sealed this
Thirtieth Day of January, 2024

Katherine Kelly Vidal
*Director of the United States Patent and Trademark Office*